United States Patent [19]

Abrutyn et al.

[11] Patent Number: 4,855,127

[45] Date of Patent: Aug. 8, 1989

[54] LATTICE-ENTRAPPED COMPOSITION

[75] Inventors: Eric S. Abrutyn, Middletown, N.Y.; Louis Scarfo, New Britain; Richard Chromecek, Litchfield, both of Conn.

[73] Assignee: Dow Corning Corporation, Midland, Mich.

[21] Appl. No.: 53,609

[22] Filed: May 20, 1987

Related U.S. Application Data

[63] Continuation-in-part of Ser. No. 882,609, Jul. 7, 1986, abandoned, which is a continuation-in-part of Ser. No. 683,603, Dec. 12, 1984, Pat. No. 4,724,240, which is a continuation-in-part of Ser. No. 246,663, Mar. 23, 1981, abandoned.

[51] Int. Cl.$^4$ .................. A61K 7/035; A61K 7/40; A61K 7/42; A61K 9/70
[52] U.S. Cl. ................... 424/411; 424/59; 424/60; 424/69; 424/78
[58] Field of Search ............ 424/78, 81, DIG. 10, 424/28

[56] References Cited

U.S. PATENT DOCUMENTS

| | | | |
|---|---|---|---|
| Re. 28,316 | 1/1975 | Banker et al. | 424/81 |
| 3,551,556 | 12/1970 | Kliment | 424/81 |
| 3,567,118 | 3/1971 | Shepherd et al. | 424/81 |
| 3,576,760 | 4/1971 | Gould et al. | 424/487 |
| 3,608,063 | 9/1971 | Banker | 424/81 |
| 3,629,392 | 12/1971 | Banker et al. | 424/81 |
| 3,660,071 | 5/1972 | Gould et al. | 424/81 |
| 3,660,563 | 5/1972 | Gould et al. | 424/81 |
| 4,283,325 | 8/1981 | Berthet et al. | 424/81 |

FOREIGN PATENT DOCUMENTS

| | | | |
|---|---|---|---|
| 1099429 | 4/1981 | Canada | 424/81 |
| 2608533 | 9/1976 | Fed. Rep. of Germany | 424/81 |
| 1336495 | 11/1973 | United Kingdom | 424/78 |

*Primary Examiner*—Dale R. Ore
*Attorney, Agent, or Firm*—Steele, Gould & Fried

[57] ABSTRACT

This invention relates to solid compositions wherein a non-cosmetic functional material is entrapped in the lattice of the cross-linked polymer during in situ polymerization of the monomers forming the polymer lattice. The invention provides for conversion of solid and/or liquid products into solid, free-flowing forms by entrapment of the functional materials in a hydrophobic polymer lattice.

14 Claims, 4 Drawing Sheets

LATTICE-ENTRAPPED COMPOSITION

RELATED APPLICATION

This is a continuation-in-part of application Ser. No. 882,609, filed July 7, 1986, now abandoned, which is a continuation-in-part of my copending application Ser. No. 683,603, filed Dec. 12, 1984, entitled "Polymer Entrapped Emollient-Moisturizer Composition," now U.S. Pat. No. 4,724,240 which in turn is a continuation-in-part of application Ser. No. 246,663, filed Mar. 23, 1981, now abandoned.

BACKGROUND AND SUMMARY OF THE INVENTION

This invention relates to solid compositions wherein a functional group is entrapped in the lattice of a cross-linked hydrophobic polymer during in situ polymerization of the monomers forming the polymer lattice. More particularly, the invention relates to comb-like polymers which have entrapped various chemicals and provide for their sustained release.

The art is replete with attempts to render functional materials amenable to release on demand through encapsulation. Encapsulation confines materials in discrete units or capsules as the result of coating particles of the material with an encapsulant. The coating wall or encapsulating material used in encapsulation includes natural or synthetic polymers which permit release of the functional material by fracture, degradation or diffusion.

*Handbook of U.S. Colorants for Food, Drugs and Cosmetics,* by Daniel M. Marmion, A. Wile. Interscience Publication, Second Edition, 1984, which is herewith incorporated by reference, discloses food flavorants and pigments which could be utilized in the present invention.

In *Pesticides: Preparation and Mode of Action* by R. Cremlyn, John Wiley and Sons Publication, 1978, and *Pesticides Guide: Registration, Classification and Applications* by J. Keller and Associates, Inc., Neenah Wisconsin, Section 167.3, 1984 which are herein incorporated by reference, disclose the various pesticides, and insect attractants which may be utilized in connection with the invention.

It is an object of the present invention to provide a novel form of entrapment of the functional material which does not encapsulate the functional material.

This invention provides a unique combination of polymers and functional materials, which results in compositions wherein the functional materials rather than being encapsulated by coating materials are dispensed throughout and entrapped within a polymer lattice. These compositions are useful for incorporating a variety of functional materials into a variety of products such as cosmetic and non-cosmetic products. Furthermore, the amount of functional materials which can be entrapped in the lattice are much higher than heretofore achievable by encapsulation.

BRIEF DESCRIPTION OF THE DRAWINGS

A better understanding of the present invention will become more apparent from the following detailed description of the invention taken in conjunction with the formal drawings, wherein.

DESCRIPTION OF THE INVENTION

Figure 1A:
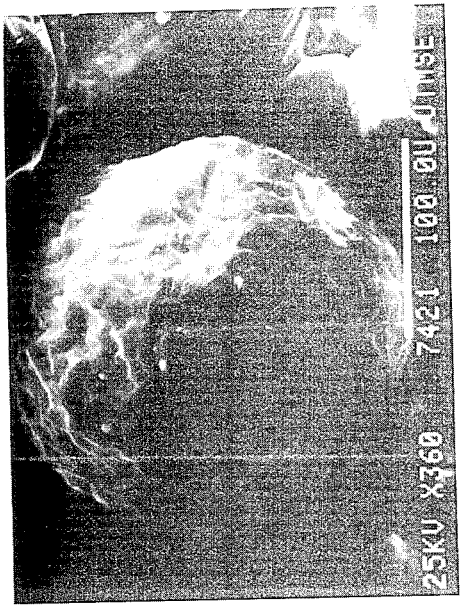
FIGS. 1A–1D are photomicrographs at increasing powers of magnification of an emollient ester entrapped in a polymer lattice.
Figure 1B:
Figure 1C:
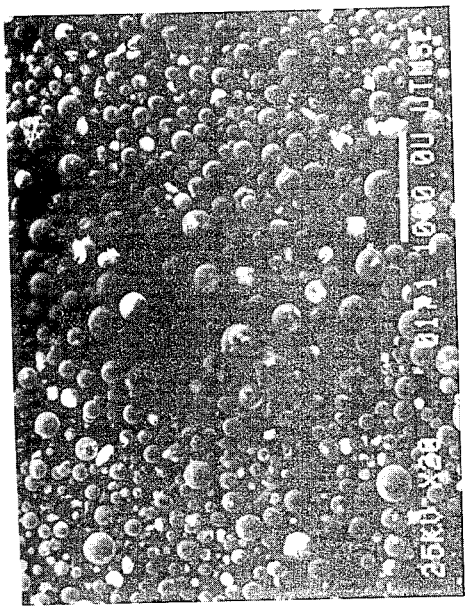
Figure 1D:
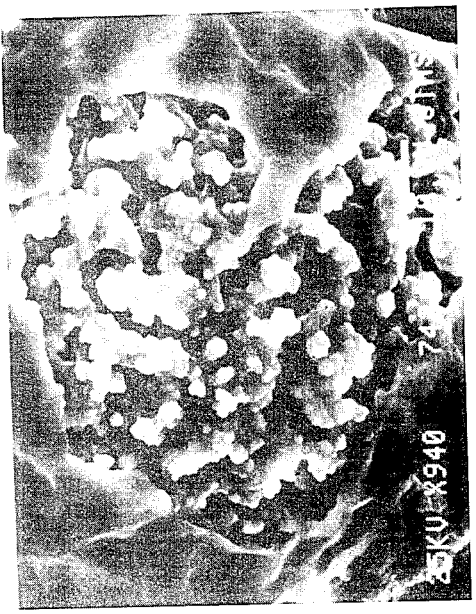

This invention relates to a solid, lattice-entrapped composition which comprises from about 5% to about 95% by weight of a cross-linked polymer lattice and from about 95% to about 5% by weight of a functional material. Unlike known methods of entrapping the functional material by encapsulating the functional material, the present invention entraps the functional material directly within the hydrophobic polymer lattice during in situ polymerization of the monomers.

It has now been discovered that a wide variety of materials which are either liquids or solids can be converted to free-flowing powders or beads by entrapment of the materials in a polymeric lattice. The entrapped materials are not themselves encapsulated in any way, i.e. enclosed by capsules, coatings or sacs; rather, they are dispersed throughout and entrapped within the polymeric lattice. Such lattice-entrapped products have properties that are superior to the encapsulated products of the prior art. The polymeric lattice functions to hold and protect the entrapped material without encapsulating it, probably through sorption or swelling, and the lattice is capable of making the material available by a variety of mechanisms including pressure, diffusion and extraction. Significantly, when the lattice-entrapped materials of this invention are incorporated into cosmetic, non-cosmetic and toiletry products the polymeric lattice itself contributes beneficial effects to the overall product structure.

According to the structure and chemical properties of the system heterogeneous or homogeneous entrapment can be achieved. If the entrapped chemical is a thermodynamically good solvent (swelling agent) for the system, a homogeneous (gel) entrapment will result. In the opposite case of a thermodynamically bad solvent, separation of phases during the polymerization will occur and a heterogeneous (macromolecular) entrapment will result.

Homogeneous or heterogeneous entrapment is naturally also dependent on the structure and amount of the crosslinker, where higher crosslinking density results in a heterogeneous product.

While this invention also shows the in situ lattice entrapment of emollient-moisturizers within the polymeric lattice, those skilled in the art will recognize that a wide variety of other functional materials can be entrapped within the polymeric lattice either alone or in combination with the emollients or moisturizers. The invention contemplates that a wide variety of water insoluble organic liquids and solids may be incorporated within the lattice. In fact, any functional material which will not chemically react with the polymer system comprising the polymeric lattice can be entrapped within the polymeric lattice.

The solid lattice-entrapped, i.e., nonencapsulated, compositions of this invention are prepared by combining in one step a functional crosslinking monomer, a monofunctional monomer and the functional material to be entrapped within the lattice under such conditions as to thereafter initiate polymerization. As used herein, the term "functional crosslinking monomer" is meant to include di- or polyfunctional monomers having two or more polymerizable double bonds, while the term "monofunctional monomer" is meant to include a polymerizable monomer having one double bond. Functional crosslinking monomers useful in the invention may be a polyunsaturated monomer selected from the group consisting of a mono- or di-ester of an alcohol and an alpha-beta unsaturated carboxylic acid; polyunsaturated polyvinyl ether of a polyhydroxy alcohol; mono- or poly unsaturated amides and cycloaliphatic esters of alpha-beta unsaturated carboxylic acids. Examples of such functional cross-linking monomers include polyethylene glycols having a molecular weight up to about 5000 dimethacrylate, triethylene glycol dimethacrylate, tetraethylene glycol dimethacrylate and trimethylol propane ethoxylated triacrylate, available under the trademark CHEMLINK®176, ditrimethylol propane dimethacrylate; propylene, dipropylene and higher propylene glycols having a molecular weight up to about 5000 including polyethylene glycol dimethacrylate, 1,3 butylene glycol dimethacrylate, 1,4 butanediol dimethacrylate, 1,6 hexanediol dimethacrylate, neopentyl glycol dimethacrylate, pentaerythritol dimethacrylate, bisphenol A dimethacrylate, divinyl (trivinyl) benzene, divinyl (trivinyl) toluene, triallyl maleate, triallyl phosphate, diallyl maleate, diallyl itaconate, and allyl methacrylate.

The monofunctional monomer of the novel polymeric system of this invention includes hydrophobic and hydrophilic monounsaturated monomers. The monomers include alkyl methacrylates and acrylates having straight or branched chain alkyl groups with 1 to 30 carbon atoms, preferably 5 to 18 carbon atoms. Preferred monofunctional monomers include lauryl methacrylate, 2-ethylhexyl methacrylate, isodecylmethacrylate, stearyl methacrylate, hydroxy ethyl methacrylate, hydroxy propyl methacrylate, diacetone acrylamide, phenoxy ethyl methacrylate, tetrahydrofurfuryl methacrylate and methoxy ethyl methacrylate.

The structure of the cross-linked polymer is characterized by layered ordering of the side chains.

The side chains separated by the backbone chains are packed in parallel layers. The backbone chains of the macromolecules are spaced by distances roughly equal to the length of the side chain.

In addition to other factors, the structure of the linkage of the side chain to the main backbone chain may vary the degree of conformation freedom at the side chain junctions. While poly alpha olefins do not have conformational freedom of the side chain segments around the C—C bond, polyacrylates and polyvinyl ethers have greater degree of freedom due to the C—O bond. The freedom of rotation of the poly methacrylates is limited by the stearic hindrance of the methyl group in the backbone chain.

The functional materials to be lattice-entrapped within the novel polymeric lattice of this invention are selected from materials which are normally either liquids or solids. Functional materials such as pigments, perfumes, pheromones, synthetic insect attractants, pesticides including juvenile hormone analogs, herbicides, pharmaceuticals, anti-microbial agents, sunscreens, light stabilizers, fragrances, flavors including sweeteners and the like, may be entrapped within the novel polymeric lattice of this invention.

The crosslinking monomer, monofunctional monomer and functional material are combined in a ratio such that the resultant novel lattice-entrapped composition of this invention comprises from about 5% to about 95% by weight of a cross-linked polymer lattice and from about 95% to about 5% by weight of the entrapped functional material. The ratio of crosslinking monomer to monofunctional monomer in the cross-linked polymer lattice can vary within the range of 99:1 to 1:99. While not restricting the invention to any precise composition, in a typical product of this invention, the crosslinking monomer, monofunctional monomer and functional material are combined in a ratio such that the resultant novel cross-linked polymer lattice comprises from about 60 to about 80% by weight of the functional material entrapped therein.

The cross-linked polymer lattice containing the entrapped functional material results from the in situ polymerization of the monomer mixture which already has the functional material to be entrapped therein. Generally, this results simply from mixing the crosslinking monomer and the monofunctional monomer, dissolving the functional material in the combined monomers to form a uniform mixture, and thereafter inducing polymerization. Polymerization may be induced by conventional initiators such as peroxides and the like, or by irradiation or redox systems. Polymerization usually occurs at temperatures between about 0° to 120° C., preferably about 80° C. The time and temperature of polymerization may be varied in accordance with the nature of the functional material, its concentration, and the attributes of the desired entrapped system, but in all instances, the polymerization occurs only after the monomers and the functional material are combined.

The physical properties of the lattice-entrapped functional materials may be influenced by several factors such as the precise combination of crosslinking monomer and monofunctional monomer selected, the ratio in which these two components are combined with one another and with the functional material. Accordingly, the lattice-entrapped materials of this invention which exist in the form of discrete, free-flowing powders or beads may be hard and have the ability to withstand rather substantial shearing, or the powders or beads may be soft, in which form they disintegrate or spread to form a uniform layer with minimal pressure. In general, the greater the ratio of cross-linked polymer lattice to the functional material, the harder the lattice-entrapped material. The lattice-entrapped functional material ranges in particle size from about 0.001 milimeters to about 3 millimeters.

A simple test has been developed to predict with reasonable accuracy whether or not a particular combination of crosslinking monomer, monofunctional monomer and functional material will polymerize to form the lattice-entrapped functional material of this invention. According to this test, approximately equal quantities of crosslinking monomer, monofunctional monomer and functional material are combined in a test tube and polymerized. If the resultant polymerized product is turbid or cloudy, a heterogeneous macroporous structure has formed which is a positive indication that the components tested can be combined in a ratio such that subsequent polymerization will result in the products of this invention. There are exceptions to this rule, in that certain combinations of materials may result in the production of a clear polymer. If, however, when the clear polymer is extracted from the reaction mixture it is determined to be cloudy or turbid, indicating a heterogeneous, macroporous structure, a positive test has again occurred. After a positive test, i.e., an initial turbid or cloudy appearance on polymerization of the test tube size sample, further tests are conducted by varying the ratio of monomers to functional material to determine those ranges in which discrete particles, and not clumps or masses, are obtained on polymerization. With the foregoing test in mind, and recognizing the need to obtain discrete particles and not clumped or massed polymers, it will be appreciated that those skilled in the art can select appropriate cross-linking monomer, monofunctional monomers and the ratio in which these materials are to be combined to obtain the lattice-entrapped materials of this invention.

The novel lattice-entrapped functional materials of this invention are versatile products having application in many and varied types of products. As stated previously, liquid and solid functional products form lattice-entrapped products which are suitable for incorporation in a wide variety of healthcare products, pesticidal agents, insect attractants, anti-microbial agents, pharmaceuticals, pesticides, disinfectants, sun screens, light stabilizers, flavors, pigments and perfumes may also be used as functional materials in the lattice-entrapped materials of this invention.

A primary advantage of formation of the novel lattice-entrapped functional materials of this invention is the conversion of liquid or solid functional materials into powdery, free-flowing materials through incorporation in a syneresis-free polymeric lattice. The lattice entrapment of the functional material provides the ability to hold the functional materials for controlled application on demand. Other advantages of the lattice-entrapping the functional materials of this invention include the ability to convert the solid and liquid functional materials into free-flowing discrete particles ranging in size from fine powders to rather large beads. Still another advantage of this invention lies in the fact that the polymer lattice itself contributes desirable attributes (discussed hereinafter) when the functional materials are entrapped therein.

The lattice-entrapped functional materials of this invention are easy to handle, convenient to store, and are prepared by relatively non-complex procedures. Lattice-entrapment of the functional materials within the cross-linked polymer lattice protects the functional materials from the environment, excessive volatilization, and from ultraviolet light. The lattice-entrapped functional materials are releasable from their entrapped state within the microscopic lattice by the application of pressure, by extraction and diffuse from the entrapped state due to temperature and humidity changes. Also, it has been found that the desirable characteristics of the lattice-entrapped functional materials, i.e. emollients and moisturizers, are enhanced by the polymer lattice itself. The polymer lattice provides a continuous film-like appearance when applied to a surface, so that the ultimate effect of the lattice-encapsulation of this invention is to extend the effect of the lattice-entrapped materials.

A decided advantage to be obtained by entrapping the functional materials according to this invention results from being able to incorporate substantially greater amounts of functional material in a desired product than is possible through incorporation of the raw functional material without lattice entrappment. For example, it is known that an emollient such as 2-ethyl hexyl oxystearate (WICKENOL ®171) provides improved moisturizing and skin softening qualities to toilet soap, but it is not possible to incorporate more than about 2–5% of such an emollient in conventional toilet soap formulations without seriously detracting from the foaming characteristics of the soap. If, however, the emollient is first formulated in the lattice-entrapped microscopic polymeric lattice of this invention, substantially higher concentrations of the emollient, up to as much as 20% by weight thereof, may be incorporated into the toilet soap formulation, thereby serving to enhance the softing and moisturizing properties of the soap without any deleterious effect on the foaming and esthetic properties of the soap. The polymer portion of the lattice also improves the mechanical properties of the soap.

Another important application for the novel lattice-entrapped functional materials of this invention is in the area of molded wax and/or oil base sticks of the type typically used for antiperspirants, deodorants, lipsticks, sun screens, topical pharmaceuticals, insect repellents, colognes, etc. Typically, these stick-type products must balance many ingredients in order to obtain the desired appearance and function, but the optimal solid wax-oil base stick seems to elude formulators because of problems such as shrinkage, variable rate of deposition, tackiness, and the like, which continue to plaque such products. The lattice-entrapped functional materials of this invention offer significant advantages to such stick-type products since they make it possible to substantially reduce the bodying agents (such as natural, vegetable or insect waxes) typically present in such stick products. These advantages result from the fact that the polymeric lattice which entraps the functional material enhances rigidity and strength of the stick while it permits the lattice-entrapped functional materials to produce their desired effect as they are made available from their lattice-entrapped state.

The lattice-entrapped functional materials of this invention are free flowing powders which are easy to handle and convenient to store. The lattice-entrapped functional materials are made available or released when applied either directly or as a component of a product. It is thought that when the entrapped functional material is applied to a surface in a cosmetic or toiletry product it is released as the result of rubbing and spreading in the form of a continuous uniform film protected within a hydrophobic envelope.

A scanning electron microscope (SEM) study was undertaken to better understand how the functional materials are entrapped in the polymer lattice. An objective of the study was to determine how miscible and immiscible functional materials differ in the manner in which they are incorporated into the polymer lattice. Additionally, the investigation showed a comparison of the lattice-entrapped product before and after a simulated application.

FIGS. 1A–1D are photomicrographs of 2-ethyl hexyl oxystearate/polymer powder (POLYTRAP ®171) entrapped in a polymer powder. The photomicrographs were taken at ×20 (FIG. 1A), ×360 (FIG. 1B), ×940

(FIG. 1C), and ×3000 (FIG. 1D) power. The photographs indicate that the ester is heterogeneously adsorbed on the surface of a very fine polymer micro-dispersion (cluster) of less than two microns in diameter. In the higher power magnifications, it can be seen that rather than being encapsulated by the polymer, the functional material is entrapped within the polymer lattice.

Figure 2A:
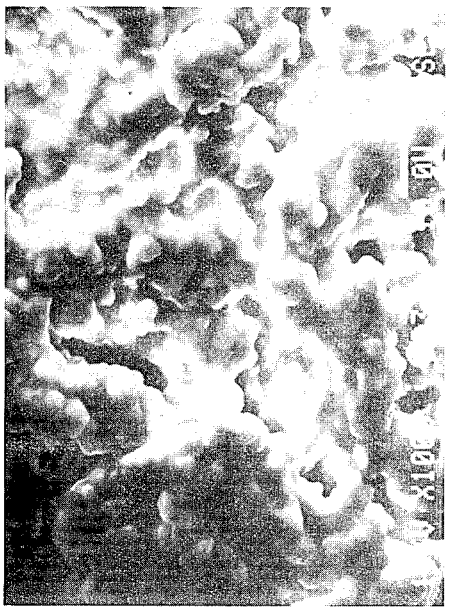
FIGS. 2A–2D show the visual effect at various degrees of magnification of a lattice-entrapped functional material product when it is applied in a thin layer.
Figure 2B:
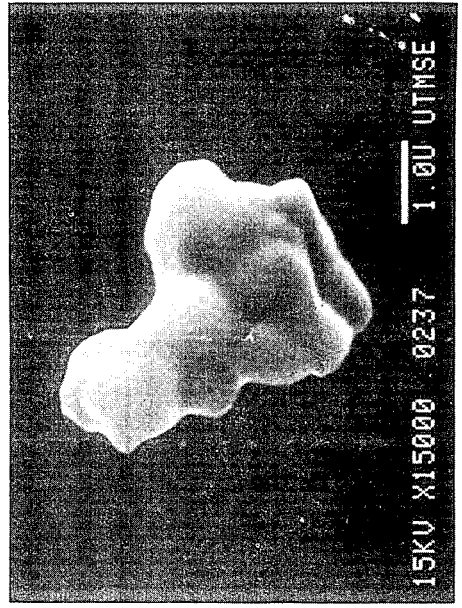
Figure 2C:
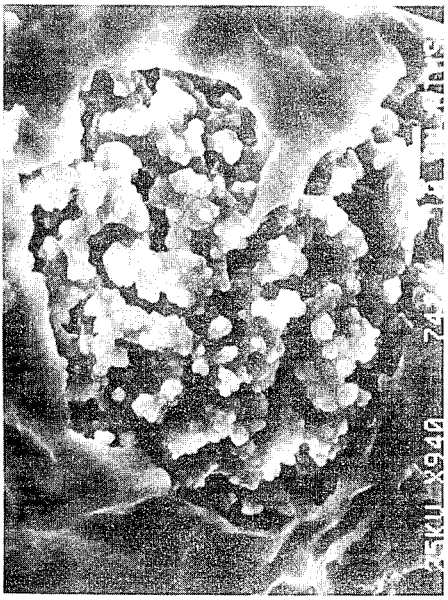
Figure 2D:

FIGS. 2A-2D show examples of a lattice-entrapped functional material product when the product is applied and spread out, such as when it is applied directly to a surface. In this series of photographs, the material is again POLYTRAP®171. FIG. 2A is an untouched photograph of the lattice-entrapped product. FIG. 2B (at ×1000) shows the lattice-entrapped film material product after it has been lightly spread. FIG. 2C (at ×1000) shows the lattice-entrapped film material product after it has been completely spread and further shows that a continuous film material results. FIG. 2D (at ×15,000) shows a more magnified view of the same product material as FIG. 2C. It can be seen from FIG. 2D that the film consists of small (less than 2 microns) particles.

Figure 3B:
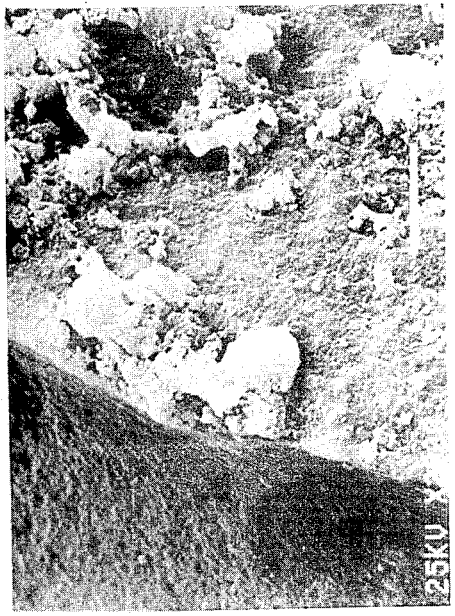
FIGS. 3A–3D are photomicrographs of lattice-entrapped functional material products wherein the functional material is a fragrance which is homogeneously miscible with the polymer.
Figure 3D:
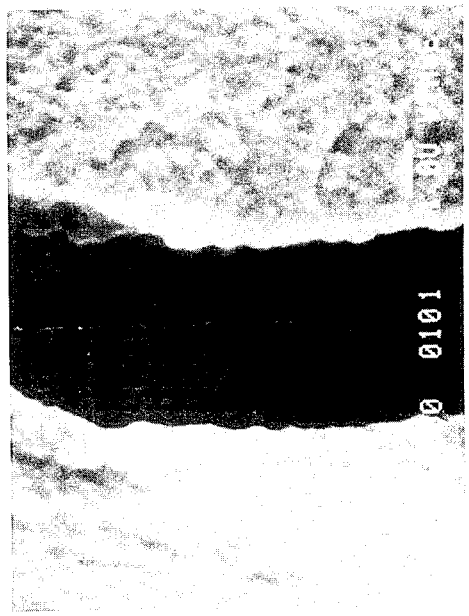
Figure 3A:
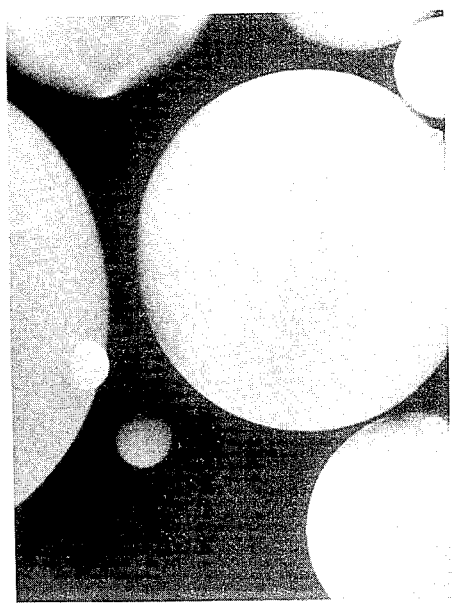
Figure 3C:
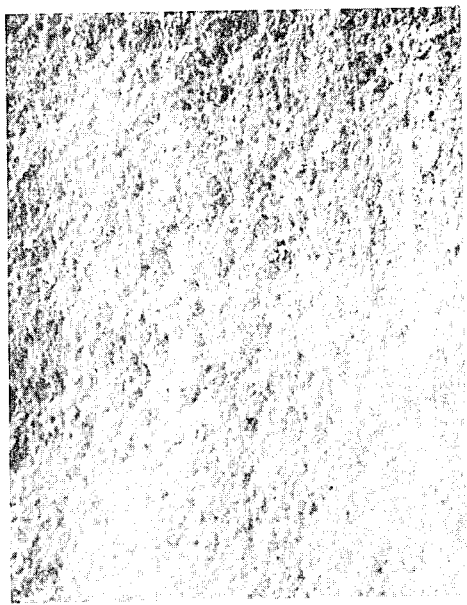

FIGS. 3A-3D are photomicrographs of the lattice-entrapped functional material product which show the incorporation of a fragrance as the lattice-entrapped functional material. Herein, the fragrance is in the form of POLYTRAP Fragrance Polymer Beads. The various photographs are taken at increasing powers of magnification, ×540 (FIG. 3A), ×2000 (FIG. 3B), ×3000 (FIG. 3C), and ×10,000 (FIG. 3D). The fragrance is homogeneously miscible with the polymer, and is therefore very evenly dispersed within the polymer lattice. This can be readily seen by comparing FIG. 3C taken at ×3,000 with the FIG. 1D which is a picture taken at the same magnification, but with the immiscible functional material in the polymer lattice. When the fragrance is homogeneously miscible with the polymer, it can be seen that an almost featureless smooth surface is created.

Figure 4A:
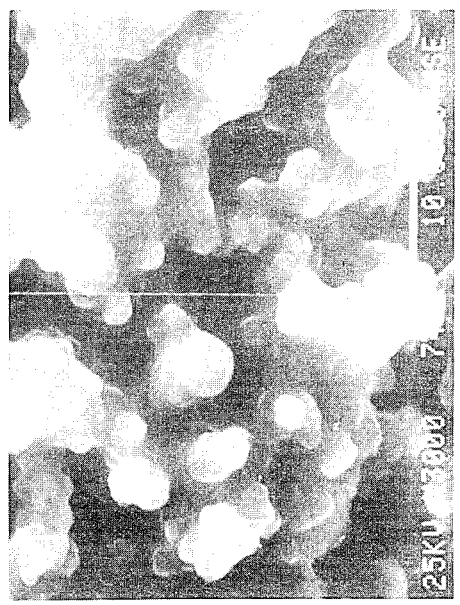
FIGS. 4A–4C are photomicrographs of a lattice-entrapped emollient; a lattice wherein the emollient has been extracted, and a polymer which is formed without functional material in the polymer lattice.
Figure 4C:
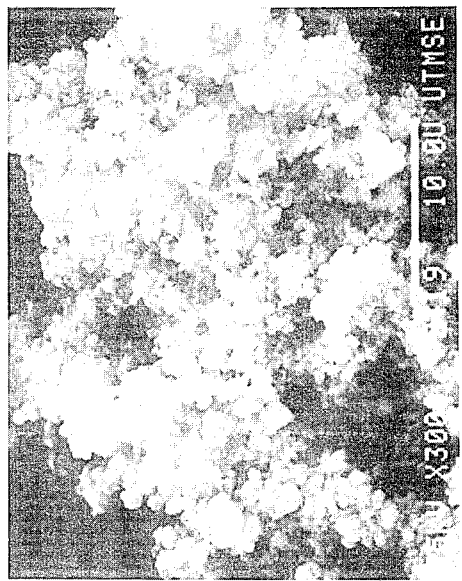
Figure 4B:
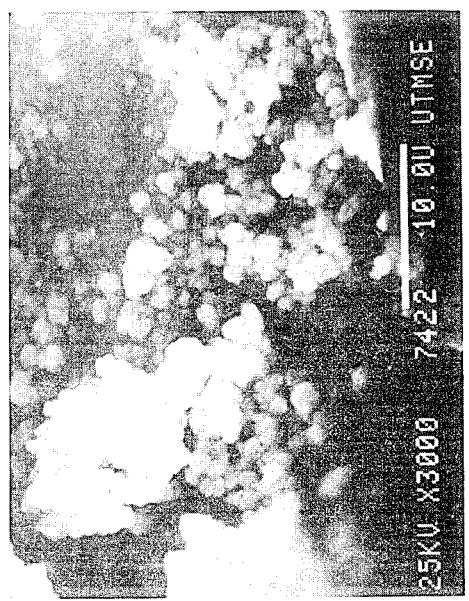

FIG. 4A shows a lattice-entrapped functional material product according to the present invention (POLYTRAP®171) at a power of ×3,000. The same product is shown in FIG. 4B; however, the lattice-entrapped emollient has been extracted therefrom. FIG. 4C is a product formed without a functional material (POLYTRAP®235) and consists simply of the blank polymer beads. FIGS. 4B and 4C are very similar.

These various scanning electron microscopy studies of the lattice-entrappment system of the invention show the effect of an entrapped species on the physical characteristics of the polymer formation. Moreover, the photographs indicate that the functional material is entrapped within the polymer lattice rather than being encapsulated by the polymer. When the functional material is miscible (e.g. fragrance) in the polymer, a homogeneous polymer lattice is formed which produces mechanically tough spheres or beads which can be milled without disturbing the integrity of the structure. When the material is a non-solvent for the polymer, a heterogeneous internal structure is formed.

The cluster of beads formed by either the miscible or immiscible functional material is fragile and when mechanical stress is applied thereto, the clusters will fracture and produce a continuous film of particle sizes less than two microns, even in the range approaching 0.1-0.2 microns.

While it will be appreciated by those skilled in the art that there are many variations in procedure and components, this invention may be illustrated by the following examples:

EXAMPLE 1

7 grams of 2 ethylhexyl oxystearate (WICKENOL®171) was mixed with 1.5 grams of ethylene glycol dimethacrylate and 1.5 grams of lauryl methacrylate in a glass test tube. The solution was deaerated for five (5) minutes and 0.1 ml of t-butyl peroctoate was added and mixed while heating to 80° C. in an oil bath. After 20 minutes, the contents solidified; and the mixture was maintained at about 80° C. for an additional hour to assure full polymerization. A semi-soft, heterogeneous white opaque polymer mass resulted containing the entrapped ester.

The following examples demonstrate initial screening of the crosslinking monomer, monofunctional monomer and functional material to determine whether or not the combination thereof will form the novel lattice-entrapped products of the invention. In each test the components were combined in a test tube and polymerization initiated and completed. Formation of an opaque polymer mass in the test tube scale test indicated that the components could be combined in large scale polymerization to form the entrapped functional materials of this invention.

EXAMPLE 2

Following the procedure of Example 1, the crosslinking monomers tetraethylene glycol dimethacrylate, trimethylol-propane trimethacrylate, trimethylol-propane ethoxy triacrylate, and allyl methacrylate were polymerized in the presence of 70% by weight 2-ethylhexyl oxystearate and 15% by weight lauryl methacrylate. In each case a semi-soft, white opaque polymer mass resulted, indicating suitability for formation of the lattice-entrapped product of this invention. Such a polymer lattice is suitable for entrapment of pharmaceutical preparations for external use, for example, wheat germ glycerides for dermatological therapy or a sunscreen preparation with p-aminobenzoic acid or its derivatives.

EXAMPLE 3

Following the procedure of Example 1, test tube polymerization was completed varying the types of monomer constituents and their ratios, and the quantity and type of functional material to be entrapped. In each instance, t-butyl peroctoate was used to initiate polymerization at a constant level of 3% by weight, based on the weight of the combined content of monomers and functional material. The components, quantity and test tube results are set forth in Table 1. The following abbreviations are used in Table I:

| | |
|---|---|
| TEGDM | Tetraethylene glycol dimethacrylate |
| TMPTM | Trimethyl propane trimethacrylate |
| EGDM | Ethylene glycol dimethacrylate |
| TPETM | Trimethylol propane ethoxylate trimethacrylate |
| LMA | Lauryl methacrylate |
| IMA | Isodecyl methacrylate |
| HMA | Hydroxyethyl methacrylate |
| DAA | Diacetone acrylamide |
| PMA | Phenoxyethyl methacrylate |
| MEMA | Methoxy ethyl methacrylate |

In the aforementioned tests it is possible to use as the functional material any of the wide variety of water insoluble liquids or solid insecticides, pesticides, sunscreens, light stabilizers, pigments, food flavorants, pheromones, synthetic attractants, pharmaceuticals, and the like, either alone or in a suitable non-aqueous solvent, for example, ethanol, mineral spirits, propylene glycol, and the like.

Suitable synthetic attractants for pest control products includes 1,1-dimethyl-4(and 5)-chloro-2-methlcyclohexane-1-carboxylate (trimedlure), medlure, siglure, butyl sorbate, cue-lure, methyl eugenol, and the like.

TABLE I

| Test No. | Cross-Linking Monomer | Weight % | Mono Funtional Monomer | Weight % | Material Entrapped | Weight % | Appearance in Test Tube |
|---|---|---|---|---|---|---|---|
| 1 | TEGDM | 67.5 | LMA | 22.5 | 2 Ethylhexyl stearate (WICKENOL ® 171) | 10 | Hard-powdery, white opaque polymer mass |
| 2 | TMPTM | 45 | IMA | 45 | Arachidyl propionate (WAXENOL ® 801) | 10 | Semi-hard, off-white opaque |
| 3 | TMPTM | 12 | IMA | 3 | Arachidyl propionate (WAXENOL ® 801) | 85 | Semi-soft, off-white opaque |
| 4 | EGDM | 18.7 | SMA | 6.3 | Di(Ethylhexyl) adipate (WAXENOL ® 158) | 75 | Semi-soft, white opaque |
| 5 | EGDM | 30 | HMA | 10.3 | Isopropyl Myristate (WICKENOL ® 101) | 60 | Semi-soft, white opaque |
| 6 | EGDM | 30 | LMA | 10 | Ethanol | 60 | Hard-powdery, white opaque |
| 7 | TEGDM | 67.5 | SMA | 22.5 | Stearyl alcohol | 10 | Very hard, white opaque |
| 8 | TEGDM | 15 | SMA | 5 | Stearyl alcohol | 80 | Hard-powdery white opaque |
| 9 | EGDM | 67.5 | DAA | 22.5 | Propylene glycol | 10 | Very hard, off-white opaque |
| 10 | EGDM | 15 | DAA | 5 | Propylene glycol | 80 | Semi-soft, off-white opaque |
| 11 | EGDM | 60 | LMA | 30 | Propionic acid | 10 | Very hard, white opaque |
| 12 | EGDM | 15 | LMA | 5 | Propionic acid | 80 | Semi-hard, white opaque |
| 13 | TEGDM | 45 | SMA | 45 | Stearic acid | 10 | Very hard, white opaque |
| 14 | TEGDM | 10 | SMA | 10 | Stearic acid | 80 | Semi-hard white opaque |
| 15 | EGDM | 67.5 | SMA | 22.5 | Polyoxy propylene (30 moles) | 10 | Very hard, white opaque |
| 16 | EGDM | 15 | SMA | 5 | cetyl alcohol (WICKENOL ® 707) | 80 | Semi-soft, white opaque |
| 17 | EGDM | 60 | DAA | 30 | Polyoxy propylene (30 moles lanolin) | 10 | Very hard, white opaque |
| 18 | EGDM | 15 | DAA | 5 | (WICKENOL ® 727) | 80 | Semi-soft, yellowish, opaque |
| 19 | TEGDM | 67.5 | LMA | 22.5 | Carbowax ® 300 | 10 | Hard and clear |
| 20 | TEGDM | 13 | LMA | 7 | | 80 | Semi-soft, white opaque |
| 21 | TPETM | 54 | PMA | 36 | Mineral oil | 10 | Hard-powdery, white opaque |
| 22 | TPETM | 15 | PMA | 15 | Mineral oil | 70 | Semi-soft, white opaque |
| 23 | TMPTM | 45 | MEMA | 45 | Petroleum jelly | 10 | Semi-soft, white opaque |
| 24 | TMPTM | 15 | MEMA | 5 | Petroleum jelly | 80 | Semi-soft, white opaque |
| 25 | EGDM | 45 | LMA | 45 | Mineral spirits | 10 | Hard powdery, white opaque |
| 26 | EGDM | 18.8 | LMA | 6.2 | Mineral spirits | 75 | Semi-hard, white opaque |
| 27 | TEGDM | 12.5 | LMA | 12.5 | Lanolin | 75 | Semi-soft, yellow opaque |
| 28 | EGDM | 60 | SMA | 30 | Poly-Hexamethyl disiloxane | 10 | Very hard, white opaque |
| 29 | EGDM | 15 | SMA | 5 | (Dow ® Q2-1096) | 80 | Hard, powdery, white opaque |
| 30 | EGDM | 60 | LMA | 30 | Poly dimethyl (cyclic) siloxane | 10 | Hard, powdery, white opaque |
| 31 | EGDM | 22.5 | LMA | 7.5 | (Dow ® 344 & 345) | 70 | Hard, powdery, white opaque |
| 32 | EGDM | 45 | DAA | 45 | Poly | 10 | Very hard, white opaque |

TABLE I-continued

| Test No. | Cross-Linking Monomer | Weight % | Mono Funtional Monomer | Weight % | Material Entrapped | Weight % | Appearance in Test Tube |
|---|---|---|---|---|---|---|---|
| 33 | EGDM | 10 | DAA | 10 | Dimethyl (Linear) Siloxane (Dow ® 200) | 80 | Semi-hard, white opaque |

The following examples demonstrate formation of the lattice-entrapped materials of this invention.

EXAMPLE 4

1.20 grams of polyvinyl pyrrolidone having a K value of about 80 to 100 and available from Dan River, Inc., was dissolved in 1500 ml of water in a 2000 ml three necked resin flask equipped with a stirrer, thermometer and nitrogen purge. A solution of 335 grams of 2 ethylhexyl oxystearate (WICKENOL ®171), 132 grams ethylene glycol dimethacrylate, 33 grams 2-ethylhexyl methacrylate and 5 ml t-butyl peroctoate was bubbled with nitrogen for 5 minutes. The resultant monomer mix was slowly added to the stirred aqueous solution of polyvinyl pyrrolidone at 22° C. under nitrogen. The temperature was raised to 80° C. with constant agitation and held until polymerization started in approximately 15 minutes, and maintained at 80° C. for an additional 2 hours to complete the reaction. Semi-soft, white opaque beads were collected by filtering off the supernantant liquid and dried to remove any excess water. The beads weighed 450 g for a yield of 90%, and were 0.25 to 0.5 mm in diameter. Other protective colloids such as starch, polyvinyl alcohol, carboxymethyl cellulose, methyl cellulose, or inorganic systems such as divalent alkali metal hydroxides, for example $Mg(OH)_2$, may be used in place of the polyvinyl pyrrolidone suspending medium. The composition is especially useful for incorporation of a pharmaceutical ingredient in combination with the ethylhexyl oxystearate for topical administration.

EXAMPLE 5

The procedure of Example 4 was repeated except that in each case 337.5 g arachidyl propionate (WAXENOL ®801), or 337.5 g mineral oil, or 350 g cyclic polydimethyl siloxane (DOW ®345), or 350 g petroleum distillate (150° to 160° C. boiling point), or 325 g petroleum jelly, or 350 g isopropyl isostearate (WICKENOL ®131), or 375 g. Di(2 ethylhexyl) adipate (WICKENOL ®158), were substituted for 2-ethylhexyl oxystearate. In each case, semi-soft, white opaque beads were collected in good yield. These beads may be incorporated into topically applied pharmaceutical products and sunscreens where they demonstrate their desired effect by making the lattice-entrapped emollient-moisturizer available for application to the skin. The particle size of the resultant bead in each case was between 0.25 to 0.5 mm in diameter. The precise particle size varied somewhat due to the degree and rate of agitation during polymerization and the rates of the components to the water in which the polymerization system was suspended.

In combination with or in lieu of any one of the functional materials mentioned in this example may be used as a suitable pharmaceutical agent for topical use or a sunscreening agent.

The following examples demonstrate compositions in which the lattice-entrapped functional materials of this invention have been incorporated.

EXAMPLE 6

| Translucent Pressed Powder | |
|---|---|
| Talc | 77.64 |
| Kaolin | 14.00 |
| 75% Arachidyl-propionate entrapped bead of Example 5 | 5.00 |
| Magnesium carbonate | 2.00 |
| Colorants | 0.31 |
| Methyl paraben | 0.10 |
| Propyl paraben | 0.10 |
| Germall 115 | 0.10 |
| Fragrance | 0.75 |
| | 100.00 |

The components were combined in accordance with conventional formulation techniques. The lattice-entrapped emollients (Example 5 product) provided a pressed powder with desired emollient properties and application of the product to the body made the emollient available by rubbing. The pressed powder was remarkably resistant to breakage crumbling and glazing.

EXAMPLE 7

| Milled Toilet Soap | |
|---|---|
| Toilet soap base of tallow and coconut[1] | 89.00 |
| 2-ethylhexyl oxystearate entrapped bead of Example 4 | 10.00 |
| Fragrance | 1.00 |
| | 100.00 |

[1]Duveen Soap Corporation, 154 Morgan Avenue, Brooklyn, New York

The components were combined in accordance with conventional formulation techniques. The lattice-entrapped emollient (Example 4) provided the soap with the desired emollient properties. In addition, the physical attributes of the soap were enhanced, rendering it more resistant to cracking in use and less brittle. The soap had excellent lathering properties.

EXAMPLE 8

| Body Powder | |
|---|---|
| Talc | 84.5 |
| Fragrance | 0.5 |
| 2-ethylhexyl oxystearate entrapped bead of Example 4 | 10.0 |
| Syloid #74 | 5.0 |
| | 100.00 |

The components were combined in accordance with conventional formulation techniques. The lattice-entrapped emollient (Example 4) provided the body powder with the desired emollient properties. In addition, the physical properties of the body powder were enhanced by providing increased adhesion to the body. The talc prior to entrapment may be combined with undecylemic acid to provide anti-fungal utility.

EXAMPLE 9

| Antiperspirant Stick | |
|---|---|
| Phase A | |
| Stearyl Alcohol | 25.0 |
| Synthetic Beeswax Flakes[a] WAXENOL ® 821 | 10.0 |
| Myristyl Myristate[a] WAXENOL ® 810 | 17.5 |
| Propylene Glycol Stearate | 12.5 |
| Phase B | |
| Aluminum chlorhydrate[a] WICKENOL ® CPS 325 | 25.0 |
| Phase C | |
| 2-Ethylhexyl oxystearate entrapped bead of Example 4 | 5.0 |
| Di-octyl adipate entrapped bead of Example 5 | 5.00 |
| | 100.00 |

[a]Wickhen Products, Inc., Huguenot, New York 12746

The antiperspirant stick formulations were prepared by heating the components of Phase A to 65°–70° C. until melted, adding the component of Phase B without further heating and with constant and continuous agitation followed by slow addition of the components of Phase C with constant agitation until a uniform mixture is obtained. The mixture was then cooled somewhat and poured into molds at temperatures of from about 50° to 55° C. The antiperspirant stick had enhanced rigidity and strength and the desired emollient properties without tackiness.

In lieu of aluminum chlorhydrate there may be added a topically active pharmaceutical agent for the treatment of dermatological disorders, i.e. corticosteroids, fluorouracil, salicylic acid, clotrimazole, zinc glycinate, and the like, or a sunscreening agent.

EXAMPLE 10

Following the procedure of Example 1, test tube polymerization was completed utilizing different pheromones and varying types of monomer constituents and their ratios. The following abbreviations are used in Table II:

| LM | n-Lauryl methacrylate |
|---|---|
| EG | Ethylene glycol dimethacrylate |
| STM | Stearyl methacrylate |
| PHE | Phenoxyethyl methacrylate |
| CHM | Cyclohexyl methacrylate |

The Pheromone sample for Podisus Maculiventris prepared in a polypropylene test tube, diameter 4.5 mm, was cut into plugs or cylinders, length 15 mm and suspended in a polycarbonate tubing.

Air was blown around the sample a 1 liter/minute at 20° C. and 10–15% of relative humidity.

The release was followed by weight loss of the sample. Constant rate period at $1.67 \cdot 10^{-5}$ g/hr. for 10 days was achieved.

Similarly the following release of pheromones was tested.

TABLE II

| PHEROMONE | CONCENTRATION IN POLYMER % | POLYMER COMPOSITION | AVERAGE RELEASE RATE g/HR. | CONSTANT RATE* PERIOD LENGTH % |
|---|---|---|---|---|
| Grandlure* | 50 | LM-EG 0.6/0.4 | $1.5 \times 15-4$ | 50 |
| Grandlure | 60 | LM-EG 0.6/0.4 | $1.5 \times 10-4$ | 55 |
| Grandlure | 80 | LM-EG 0.6/0.4 | $1.8 \times 10-4$ | 70 |
| Grandlure | 50 | LM-EG 0.8/0.2 | $2.10-4$ | 60 |
| Grandlure | 50 | STM-EG 0.8/0.2 | $2.5 \times 10-4$ | 65 |
| Trimedlure | 70 | PHE-EG 0.8/0.2 | $2.5 \times 10-4$ | 70 |
| Trimedlure | 50 | CHM-EG 0.8/0.2 | $1.10-4$ | 50 |
| Trimedlure | 60 | CHM-EG 0.8/0.2 | $1.10-3$ | 60 |
| Trimedlure | 70 | CHM-EG 0.8/0.2 | $1.10-4$ | 70 |
| Methyl Eugenol | 50 | LM-EG 0.4/0.6 | $6.10-4$ | 60 |
| Methyl Eugenol | 50 | PHE-EG 0.4/0.6 | $6.10-4$ | 60 |
| Methyl Eugenol | 50 | PHE-EG 0.8/0.2 | $8.10-4$ | 65 |
| Cuelure-Malathion | 60 | CHM-EG 0.4/0.6 | $1.2 \times 10-4$ | 60 |

*Cis-2-isopropenyl-1-methyl-cyclobutane-ethanol (30% Racemic)
*The length of the constant rate period was determined as inflection point where the falling rate period begins.

EXAMPLE 11

DIAZINON (O.O Diethyl-O-(2-isopropyl-4-methyl)thiophosphate), a pesticide, was entrapped in a system of LM 0.2/EG0.8 mol. ratio. The amount of Diazinon was varied from 50 to 80%. The polymerization was performed at 80° C. under nitrogen as in Example 10 (Pheromones). In each instance, clear homogeneous articles were obtained.

Similar procedures were used for several pesticides listed in Table III.

TABLE III

| COMPOUND | % ENTRAPPED | MONOMERS/MOL RATIO | | PRODUCT |
|---|---|---|---|---|
| S,S Dipropyl-O—Ethyl Phosphodithionate (ETHOPROP) | 50 | LM 0.5 | EG 0.5 | Clear, Hard |
| N,N Dimethyl Dodecyl | 50 | LM 0.7 | EG 0.3 | Clear |
| | 50 | LM 0.6 | TETRA 0.4 | Opaque |
| N,N Diethyl m-Toluamide (DEET) | 70 | LM 0.8 | EG 0.2 | Clear, Elastic |
| N—Methyl N—(3Tolyl) | 50 | BM 0.8 | EG 0.2 | Clear, Hard |

TABLE III-continued

| COMPOUND | % ENTRAPPED | MONOMERS/MOL RATIO | | PRODUCT |
|---|---|---|---|---|
| Thiono Carbamate (TINACTIN) | 50 | LM 0.8 | EG 0.2 | Opaque, Hard |
| 3-Phenoxy-Benzyl-d-cis Trans Chrysantemate (SUMITHRIN) | 50 | LM 0.8 | EG 0.2 | Clear, Brittle |
|  | 50 | LM 0.5 | EG 0.2 | Sl. Opaque, Hard |
|  | 50 | PHE 0.8 | EG 0.2 | Opaque, Hard |
|  | 50 | CHM 0.8 | EG 0.2 | Clear, Hard |
|  | 50 | BM 0.8 | EG 0.2 | Sl. Opaque, Hard |
| 0,0-Diethyl-0-(3,5,6 Trichloro-2 Pyridyl) Phosphonthionate (CHLORPYRIFOS) | 50 | LM 0.8 | EG 0.2 | Sl. Opaque, Hard |
|  | 50 | LM 0.6 | EG 0.4 | Clear, Brittle |
|  | 60 | LM 0.6 | EG 0.4 | Clear, Brittle |
| 2,2 Dimethyl-3-(3 Methyl -5 (4-Methyl Ethyl-Phenoxy) 3 Pentenyl) OXIRANE | 50 | LM 0.8 | EG 0.2 | Clear, Brittle |
|  | 50 | DAA 0.8 | EG 0.2 | Clear, Hard |
| 2,4,4'Trichloro-2'Hydroxy Dipenyl Oxide (IRGASAN DP 300) | 50–70 | LM 0.9 | EG 0.1 | Clear, Hard |
| 2,4 Dibromo Salicyl 4'Bromoanilide (TEMASEPT) | 50 | VP 0.9 | EG 0.1 | Clear, Hard |
| (5 Benzyl-3-Furyl) Methyl-2,2-Dimethyl-3 (2 Methyl Propenyl Cyclopropane Caboxylate (SPB 1382) | 50 | LM 0.7 | EG 0.3 | Clear, Brittle |
| O,O—Dimethyl-S—(N—Methyl Carbamoyl Methyl) Phosphorodithionate (DIMETHOATE) | 50 | LM 0.5 | EG 0.5 | Opaque, Hard |
| 0,0-Diethyl-S—[(Ethyl Thio) Methyl] Phosphoro Dithionate (PHORATE) | 50 | LM 0.5 | EG 0.5 | Clear, Hard |
| 0,0 Dimethyl-S—(1.2 Dicarbethoxyethyl) Dithionate (MALATHION) | 50–80 | LM 0.2–0.8 | EG 0.8–0.2 | Clear, Hard |
|  | 50–80 | PHE 0.4–0.8 | EG 0.6–0.2 | Clear, Hard |
| 1,2 Dichlorovinyl Dimethyl Phosphate (DDVP) | 80 | LM 0.8 | EG 0.2 | Clear, Elastic |
| 1-2-Allyl-4Hydroxy-3-Methyl-2-Cyclopenten-1-One Ester of Trans Chrysanthemum Monocarboxylic Acid (d-TRANS-ALLETHRIN) | 50–70 | LM 0.8–0.5 | EG 0.2–0.5 | Clear, Soft Hard |
| Isopropyl (2E-4E)-11-Methoxy-3,7,11-Trimethyl-2,4 Dudecadenoate (METHOPRENE) | 50–70 | LM 0.8–0.5 | EG 0.2–0.5 | Clear, Soft Hard |
| Pyrethrins | 50–80 | LM 0.8–0.2 | EG 0.2–0.8 | Clear, Hard |
| Bis(Tri-n-Butyl) Tin Oxide | 50 | LM 0.8–0.2 | EG 0.2–0.8 | Clear to Opaque Hard |
| 1-(4-(1.1 Dimethyl Ethyl henoxy) Cyclohexyl 2-Propynyl Sulfite (OMITE) | 50 | LM 0.8–0.2 | EG 0.2–0.8 | Clear, Elastic to Hard |
| 2-[Trichloromethyl Thio] ntalimide [Folpet] | 10–60 | LM 0.8–0.2 | EG 0.2–0.8 | Opaque |

EXAMPLE 12

62.5 g of d-trans Allethrin, 15.51 of Lauryl Methacrylate 49.9 g of Tetraethylene Glycol Dimethacrylate and 1.25 g of Dibenzoyl Peroxide were suspended under stirring in 375 ml of deionized water containing 0.3 g of polyvinyl Pyrrolidone D-90. The suspension was heated gradually to 80° C. After formation of solid beads, the suspension was heated another 2 hours at 85° C. The beads were filtered and air dried. Similar procedures using different monomers their ratio and ratios monomers/pesticides was used in preparation of other pesticides in bead form.

EXAMPLE 13

P-methoxy bensaldehyde, a fragrance, was entrapped in a system LM 0.8/EG 0.2 mol. in concentrations 10–80% using the procedure as in Example 10 (Pheromones). Clear products were obtained.

The same procedure was applied to several other fragrance components listed in Table IV.

Similarly, total fragrance formulations of unknown composition were entrapped in concentrations 10–80%.

Suspension polymerization rendering bead form was performed the same way as described in pesticides and pheromones.

TABLE IV

| COMPOUND | % ENTRAPPED | MONOMERS/MOL RATIO | | PRODUCT |
|---|---|---|---|---|
| n-Methoxybenzaldehyde (AUBEPINE) | 10–80 | LM 0.2–0.8 | EG 0.2–0.8 | Clear, Solid |
| n-Cyano-Methoxyphenol Aubepine Nitrile | 10–80 | LM 0.2–0.8 | EG 0.2–0.8 | Clear, Solid |
| Eugenol | 10–50 | LM 0.2 | TETRA 0.8 | Clear, Solid |
| Isoeugenol | 10–50 | LM 0.2 | TETRA 0.8 | Clear, Elastic |
| Methoxy 4 Methyl | 10–50 | LM 0.2 | TETRA 0.8 | Clear, Solid |

TABLE IV-continued

| COMPOUND | % ENTRAPPED | MONOMERS/MOL RATIO | | PRODUCT |
|---|---|---|---|---|
| Phenol-2 | | | | |
| Fir Needle Oil Siberian | 10–50 | LM 0.2 | TETRA 0.8 | Clear, Solid |
| Ethyl Safranate (Safran) | 10–50 | LM 0.2 | TETRA 0.8 | Clear, Solid |
| Thuja Oil | 10–50 | LM 0.2 | TETRA 0.8 | Clear, Solid |
| Vetiver Oil Boubbon | 10–50 | LM 0.2 | TETRA 0.8 | Clear, Elastic |
| Methyl Anthranilate | 10–50 | LM 0.2 | TETRA 0.8 | Clear, Solid |
| Dimethyl Anthranilate | 10–50 | LM 0.2 | TETRA 0.8 | Clear, Solid |
| Indole | 10–50 | LM 0.2 | TETRA 0.8 | Clear, Solid |
| Geranyl Acetate | 20–80 | LM 0.2–0.8 | EG 0.8–0.2 | Clear, Solid |
| Benzyl Acetate | 20–80 | LM 0.2–0.8 | EG 0.8–0.2 | Clear, Solid |
| Anthracine 08 | 10–50 | LM 0.2 | TETRA 0.8 | Clear |
| Dihydro Myrcenol | 10–50 | LM 0.2 | TETRA 0.8 | Opaque |
| Linallyl Acetate | 10–60 | LM 0.2 | TETRA 0.8 | Opaque |
| Phenyl Ethyl Alcohol | 10–80 | LM 0.2 | TETRA 0.8 | Clear |
| Methyl Cinnamate | 10–70 | LM 0.2 | TETRA 0.8 | Opaque |
| Terpineol | 10–60 | LM 0.2 | TETRA 0.8 | Opaque |
| Diethyl Phtalate | 10–70 | LM 0.2 | TETRA 0.8 | Clear |
| Benzyl Salicylate | 10–60 | LM 0.2 | TETRA 0.8 | Clear |
| Benzyl Benzoate | 10–60 | LM 0.2 | EG 0.8 | Opaque Hard |

EXAMPLE 14

Several chemicals used in different fields of applications such as emollients, esters, sunscreens, siloxanes, etc., were entrapped using the procedure described in Example 10 (Pheromones). Details of the entrapment are given in Table V.

TABLE V

| COMPOUND | % ENTRAPPED | MONOMERS/MOL RATIO | | PRODUCT |
|---|---|---|---|---|
| Menthol | 60 | CHM 0.8–0.2 | EG 0.2–0.8 | Hard, Clear |
| | 75 | STEM 0.7 | EG 0.3 | Clear, Soft |
| Soybean Oil | 50 | STEM 0.6 | EG 0.4 | Clear, Soft |
| d-Limonene | 50 | LM 0.8 | EG 0.2 | Clear, Elastic |
| | 50 | LM 0.6 | EG 0.2 | Clear, Hard |
| | 50 | LM 0.5 | EG 0.5 | Clear, Hard |
| Methyl Nonyl Ketone | 50 | LM 0.8 | EG 0.2 | Clear, Brittle |
| | 50 | LM 0.5 | EG 0.5 | Opaque, Hard |
| Cinnamic Aldehyde | 50 | LM 0.8 | EG 0.2 | Clear, Soft |
| | 50 | LM 0.5 | EG 0.5 | Clear, Hard |
| Vitamin E | 55–75 | LM 0.3 | EG 0.7 | Opaque, Hard to Soft |
| Di(2-Ethylhexyl) Adipate | 60–80 | LM 0.3 | EG 0.7 | Opaque, Hard to Soft |
| Myristyl Lactate | 80–85 | LM 0.3 | EG 0.7 | Opaque, Soft |
| 2-Ethylhexyl Palmitate | 65 | LM 0.3 | EG 0.7 | Opaque, Soft |
| Octyl Salicylate | 20–60 | LM 0.2 | EG 0.8 | Opaque, Soft |
| Dimethylamino Benzoic Acid Pentyl Ester (ESCALOL 506) | 20–60 | LM 0.2 | EG 0.8 | Clear, Solid |
| n-Dimethylamino Benzoic Acid 2-Ethylhexyl Ester | 20–60 | LM 0.2 | EG 0.8 | Clear, Solid |
| 2Hydroxy-4 Methoxy-Benzophenone (OXYBENZONE) | 20–60 | LM 0.2 | EG 0.8 | Clear, Solid |
| Salicylic Acid | 50 | HM 0.6 LM 0.2 | TETRA 0.2 | Opaque, Hard |
| Methyl Salicylate | 60 | IBOMA 0.7 | EG 0.3 | Clear, Hard |
| 1,8,9 Anthralene Triol and Mineral Oil | 60 | LM 0.2 | EG 0.4 | Opaque, Hard |
| 2,6,10,15,19,23 Hexammethyl Tetra Cosane (SQUALANE) | 25–60 | -DEC 50 | EG 50 | Clear, Soft |
| | 25–60 | CHM 50–75 | EG 50–25 | Clear, Hard to Soft |
| | 25–60 | STEM 50–80 | EG 50–20 | Opaque, Soft |
| Simethicon Straight Chain Poly-Siloxane | 60 | STEM 40 | EG 60 | Opaque, Soft |
| Dimethyamino Oleate | 50 | STEM 0.8–0.5 | EG 0.2–0.5 | Clear, Soft |
| Decamethyl Cyclo Penta Siloxane | 60–70 | STEM 0.6–0.7 | EG 0.4–0.3 | Opaque, Hard to Soft |
| Dimethyl Laurylamine Oleate | 35–50 | STEM 0.5–0.6 | EG 0.4–0.5 | Opaque, Soft |
| Mineral Oil | 45–60 | STEM 0.6 | EG 0.4 | Opaque, Soft |
| Pentalyn H in Isopar G | 50–70 | STEM 0.5–0.7 | EG 0.5–0.3 | Opaque, Soft |
| 2-Ethylhexyl Oxystearate (WICKENOL 171) | 70 | STEM 0.8 | EG 0.2 | Clear, Soft |
| Isopropyl Isostearate (WICKENOL 131) | 67 | STEM 0.8 | EG 0.2 | Opaque, Soft |
| Octyl Dodecyl Myristate (WICKENOL 142) | 60 | STEM 0.8 | EG 0.2 | Clear, Soft |
| Isopropyl Myristate | 70 | LM 0.95–0.05 | EG 0.05–0.95 | Clear to Opaque |

TABLE V-continued

| COMPOUND | % ENTRAPPED | MONOMERS/MOL RATIO | | PRODUCT |
| --- | --- | --- | --- | --- |
| | | | | Soft to Hard |
| Soybean Oil | 50 | STEM 0.6–0.8 | EG 0.4–0.2 | Clear, Elastic |
| Bisabolol Racemic | 25 | STEM 0.4 | EG 0.6 | Clear, Hard |
| | 25 | CHM 0.8–0.4 | EG 0.2–0.6 | Clear, Hard |
| Tetrakis (2 Chloroethyl) Ethylene Diphosphate (Thermolin 101) | | LM 0.2 | EG 0.8 | Hazy Soft |
| Bromochlorinated Paraffin | | LM 0.8–0.2 | EG 0.2–0.8 | Clear, Soft to Hard |

Similarly, other chemicals and combinations were entrapped:
Benzophenone and 2-ethylhexyl oxystearate (1:1 nt)
Oleylalcohol and glycerine esters
Petroleum distillate and glycerine esters
Petroleum distillate
Jojoba Oil
Citrus Oil

What is claimed is:

1. A solid pheromone entrapped composition comprising:
   from approximately 5% to approximately 95% by weight of a cross-linked hydrophobic comb-like polymer lattice;
   from approximately 95% to about 5% by weight of a solid pheromone;
   said monomers of said cross-linked polymer and said pheromone being polymerized in situ;
   said pheromone being dispersed uniformly throughout and entrapped within said polymer lattice.

2. The composition as claimed in claim 1, wherein said cross-linked polymer matrix comprises:
   a functional cross-linking monomer selected from the group consisting of a difunctional monomer having at least two polymerizable double bonds and a polyfunctional monomer having at least two polymerizable double bonds; and
   a monofunctional monomer selected from the group consisting of polymerizable monomers having one double bond.

3. The composition as claimed in claim 2, wherein said polyfunctional cross-linking monomer is a polyunsaturated monomer selected from the group consisting of a monoester of a monovalent alcohol, a monoester of a divalent alcohol, a monoester of a polyvalent alcohol, a diester of a monovalent alcohol, a diester of a divalent alcohol, a diester of a polyvalent alcohol, a polyester of a monovalent alcohol, a polyester of a divalent alcohol, a polyester of a polyvalent alcohol, and alpha-beta unsaturated carboxylic acid, polyunsaturated polyvinyl ether of a polyvalent alcohol, monosaturated amides polyunsaturated amides and cycloaliphatic esters of alpha-beta unsaturated carboxylic acids.

4. The composition as claimed in claim 2, wherein said monofunctional monomer is selected from the group consisting of hydrophobic monounsaturated monomers and hydrophylic monounsaturated monomers.

5. The composition as claimed in claim 1, including a pesticidal agent.

6. The composition as claimed in claim 5 wherein said pesticidal agent is a juvenile hormone analog.

7. The composition as claimed in claim 1 wherein said composition comprises free-flowing powders.

8. The composition as claimed in claim 1 wherein said composition comprises free-flowing beads.

9. The composition as claimed in claim 1 wherein said composition comprises a plug.

10. The composition as claimed in claim 1 wherein said plug is in cylinder form.

11. The composition as claimed in claim 4 wherein said monomers are alkyl methacrylates and arcylates having straight or branch chain alkyl groups with 1 to 30 carbon atoms.

12. The composition as claimed in claim 11 wherein said monomers are selected from the group consisting of lauryl methacrylate, 2-ethylhexyl methacrylate, isodecylmethacrylamide, diacetone acrylamide and methoxy ethyl methacrylate.

13. The composition of claim 1 wherein said pheromone is cis-2-isopropylpentyl-1-methyl-cyclobutane-ethanol.

14. The composition of claim 1 wherein said pheromone is 1,1-dimethyl-chloro-2-methyclclohexane-1-carboxylate.

* * * * *